Figure 3:
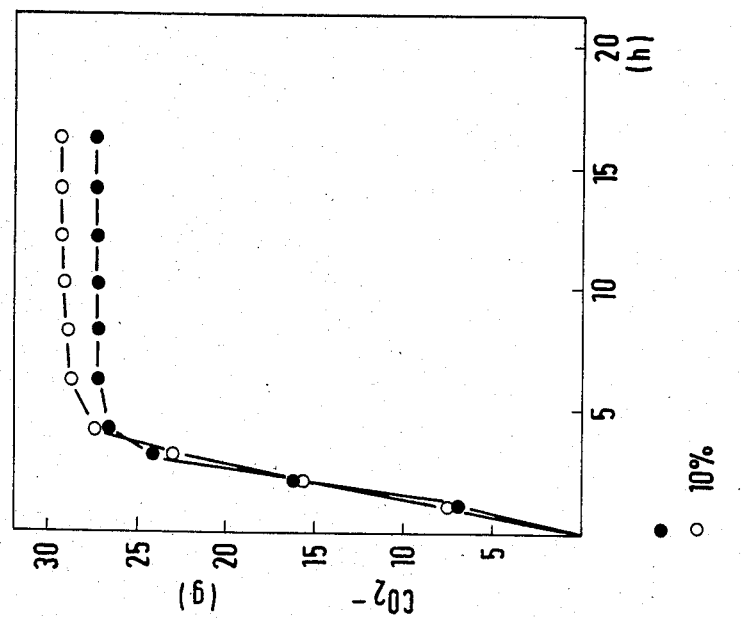
Figure 2:
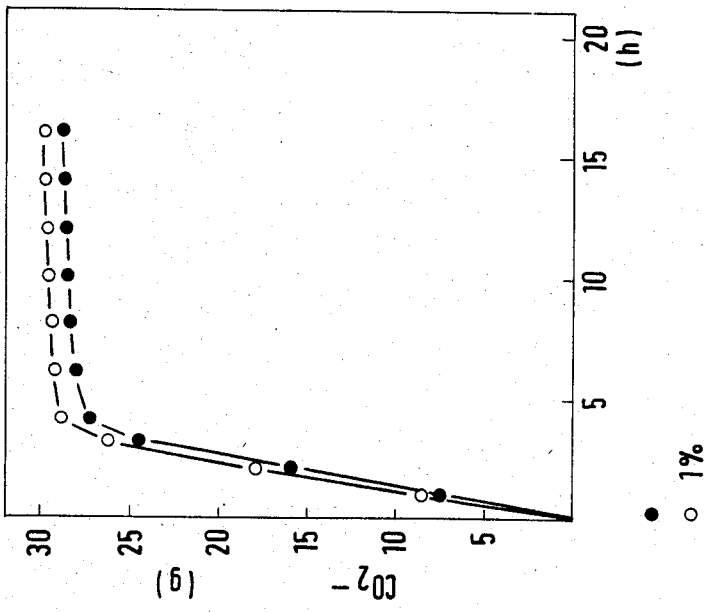

United States Patent [19]
Brückner

[11] Patent Number: 4,578,525

[45] Date of Patent: Mar. 25, 1986

[54] PROCESS FOR EXTRACTING POLAR ORGANIC COMPOUNDS, IN PARTICULAR LOWER ALIPHATIC ALCOHOLS, FROM THEIR AQUEOUS SOLUTIONS, AND FLUIDS PARTICULARLY SUITABLE FOR THIS PURPOSE

[75] Inventor: Harald Brückner, Berlin, Fed. Rep. of Germany

[73] Assignees: Krupp Industrietechnik Werk Buckau-Wolf, Grevenbroich; Starcosa GmbH, Brunswick; Versuchs- und Lehranstalt für Spiritusfabrikation und Fermentationstechnologie in Berlin, Berlin, all of Fed. Rep. of Germany

[21] Appl. No.: 535,879

[22] Filed: Sep. 26, 1983

[30] Foreign Application Priority Data

Sep. 30, 1982 [DE] Fed. Rep. of Germany ..... 32364962

[51] Int. Cl.$^4$ ...................... C07C 29/86; C07C 31/08; C07C 45/80

[52] U.S. Cl. .................... 568/918; 252/60; 568/411; 568/606; 568/608; 568/609; 568/623; 568/630; 568/660; 568/664; 568/679

[58] Field of Search ................. 568/918, 411

[56] References Cited

U.S. PATENT DOCUMENTS

2,658,069 11/1953 van der Waals .................... 568/918
4,424,388 1/1984 Braithwaite et al. ............... 568/918

FOREIGN PATENT DOCUMENTS

2305021 8/1973 Fed. Rep. of Germany ...... 568/918

Primary Examiner—J. E. Evans
Attorney, Agent, or Firm—Ladas & Parry

[57] ABSTRACT

A process is presented for extracting polar organic compounds, in particular lower aliphatic alcohols, out of their aqueous solutions, which is based on the use of fluids which contain a significant amount of polyoxaalkanols, polyoxaalkanediols and/or polyoxaalkanepolyols. These compounds, by virtue of their high molar masses, their low solubility in water and their good affinity for polar organic compounds, are particularly suitable for use as extractants.

17 Claims, 3 Drawing Figures

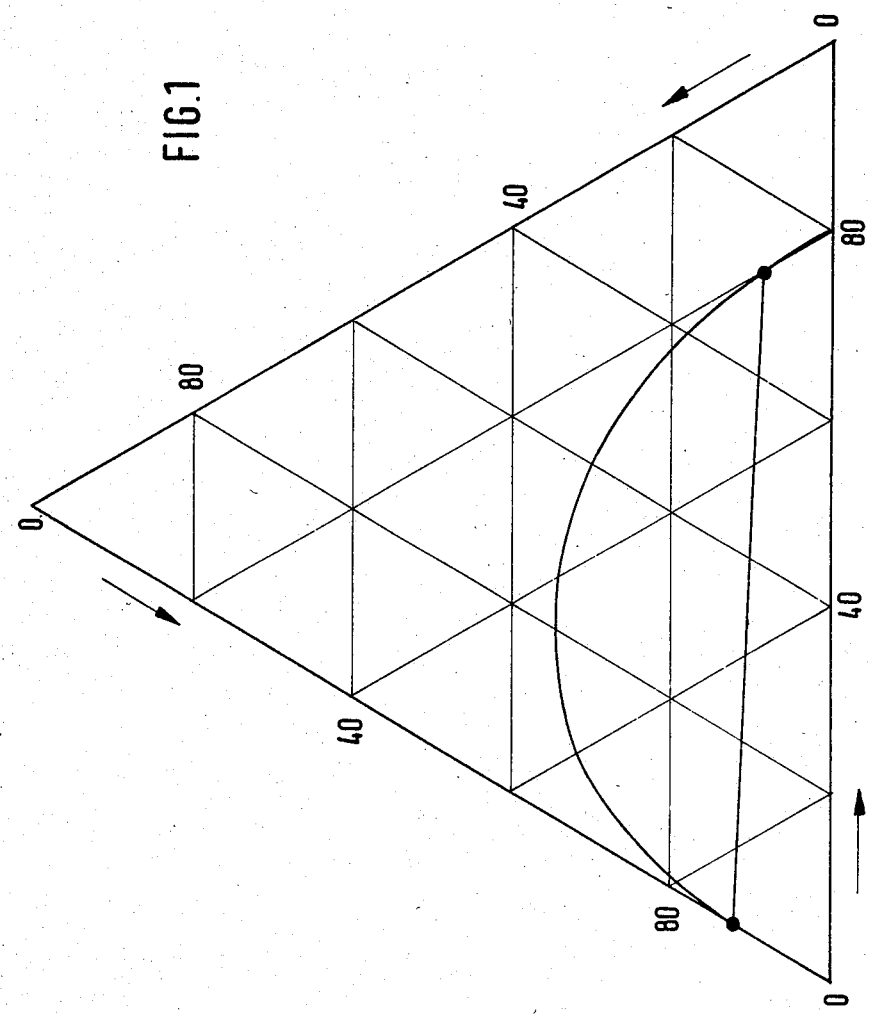

PROCESS FOR EXTRACTING POLAR ORGANIC COMPOUNDS, IN PARTICULAR LOWER ALIPHATIC ALCOHOLS, FROM THEIR AQUEOUS SOLUTIONS, AND FLUIDS PARTICULARLY SUITABLE FOR THIS PURPOSE

The invention relates to a process for extracting polar organic compounds out of aqueous solutions, suspensions, dispersions and emulsions (referred to below as "aqueous solution"), and in particular for separating off ethanol and other lower aliphatic alcohols as produced, for example, in industrial fermentation. The essence of the invention consists in using specially structured fluid compounds which have been equipped with properties particularly favourable for the intended use, for extracting polar organic compounds, such as, for example, lower aliphatic alcohols, out of their aqueous solutions. In providing these new solvents or extractants, the invention opens up a new, improved way of isolating these polar organic compounds by extraction. This applies in particular to the extraction of such compounds as ethanol, butanol and acetone, which form on fermentation of aqueous carbohydrate solutions, i.e. which are produced microbiologically.

The use of the fluids of the invention affords particular advantages in that, on the one hand, the relatively high molar masses of the extractants enable the extracts obtained to be worked up by means of a membrane-separating process, and, on the other, that because the fluids have no toxic effects, the polar organic compounds can also be separated from mashes without having to separate off beforehand the microorganisms effecting the fermentation.

In the state of the art, polar organic compounds, which include, inter alia, methanol, ethanol, propanol and acetone, are separated from their aqueous solutions almost exclusively by distillation, which, however, is a relatively expensive method in terms of energy consumption.

As a consequence of the increased cost of energy and the foreseeable scarcity of fossil energy carriers, ways of utilising regrowing energy carriers are being increasingly sought. For instance, the production of methanol, butanol and acetone, but in particular that of ethanol, from renewable carbohydrate-containing raw materials has recently attracted interest—witness the research and energy policies of numerous countries.

In utilising such compounds, which can be used as raw materials for industry and as engine fuels, it is particularly desirable to reduce the required energy input until a positive energy balance is achieved. A starting point for achieving this object is to replace the distillative purification of these organic compounds by a less expensive physical method.

Extraction is regarded as the alternative to distillation.

If there is as yet no industrially utilised extraction method for separating polar organic compounds such as, for example, ethanol, from their aqueous solutions, this is mainly due to the lack of a solvent especially suitable for this purpose, for suitable extraction equipment of various embodiments are sufficiently well known, cf. Ullmann Enzyklopädie der Technischen Chemie [Ullmann's Encyclopaedia of Industrial Chemistry], Volume II, page 560, published by Verlag Chemie Weinheim, 1972 (Ivth edition); and Perry/Chilton "Chemical Engineers' Handbook", Section 15, 5th edition, McGraw Hill, New York, 1973. The invention too wishes to make use of such extraction equipment known per se.

It is a primary object of the invention to provide an inexpensive process for separating polar organic compounds, in particular lower aliphatic alcohols, from their aqueous solution by extraction with liquid extractants which, by virtue of their structural and other physical properties, are so designed as to allow the intended process to be carried out not only more simply but combined with the subsequent recovery of the extracted component(s), also more favourably overall. Another object is a separating process which, in addition to the general advantages achieved by the invention, makes it unnecessary to separate off the microorganisms effecting the fermentation.

The invention provides extractants which are particularly suitable for said purposes in the form of fluids and proposes an extracting process which is distinguished by the use of specially structured extractors (chemical compounds), namely liquid polyoxaalkanols, polyoxaalkanediols and relatively polymeric polyoxaalkanepolyols having further defined structural and physical properties.

According to the present invention it provides a process for separating polar organic compounds, in particular lower aliphatic alcohols, from their aqueous solutions by extracting the aqueous solution with a liquid extractant and separating the polar organic compound from the extract, wherein the aqueous solution is extracted with at least one liquid polyoxaalkanol, polyoxaalkanediol and/or polyoxaalkanepolyol which has a low solubility in water, namely of less than 1% by mass, and a parameter, $K_Z$, which has a numerical value of at least 100 and is defined by the following equation:

$$K_Z = \frac{M}{\sqrt{2o + oh}}$$

in which "M" denotes the molar mass, "o" denotes the number of ether groups and "oh" denotes the number of hydroxyl groups, and in which compounds the numerical ratio of —CH(A)— groups to ether groups is within the range from about 2.3:1 to 10:1, where A represents hydrogen, $CH_3$ and/or OH.

It further provides a fluid useful in this process which contains a significant amount of at least one liquid polyoxaalkanol, polyoxaalkanediol and/or polyoxaalkanepolyol having (a) a low solubility in water at 30° C., namely of less than 1% by mass,
(b) a molar mass of greater than 250 g/mol,
(c) the general formula $$Y'—O—X—O—Y''$$

in which
x is an at least dimeric polyalkylene or polyoxyalkylene radical which has a total of 2 to about 140 carbon atoms in the skeleton chain and which has been substituted by one or more hydroxyl groups, alkoxyl groups and/or hydroxyalkoxyl groups which each have 1 to about 7 carbon atoms and/or glycidyl groups and is optionally additionally substituted by one or more lower alkyl groups and in which the individual alkylenes of the polyoxyalkylene radical can be identical or different and contain 2 to 6 carbon atoms, and Y' and Y" can be identical or different and independently of each other denote alkyl groups having 1 to 12 carbon atoms and/or cycloalkyl groups having 3 to 10 carbon atoms and/or aryl groups having 6 to 14 carbon atoms, and (d) a numerical ratio of —CH(A)— groups to the ether groups within the range from about 2.3:1 to 10:1, where A denotes the radicals H, $CH_3$ and/or OH.

The fluids of the invention have been found to be particularly suitable for these purposes. Preferably the extraction is carried out at a temperature in the range 25° C. to 120° C. Desirably the polar organic material is separated from the extracting solvent without the use of a thermal separating process, preferably using a membrane-separating process. The process is particularly useful in separating materials such as ethanol or other alcohols from a continuous or discontinuous fermentation the depleted solution being returned to the fermentation vessel. In this case there is no need to separate out the microorganisms used in the fermentation before carrying out the extraction.

Particularly useful compounds in fluids according to the invention are those of the formulae $R^5$ is hydrogen or methyl, "d" is an integer from 2 to 6, "e" is an integer from 1 to 7, and "f" is an integer from 0 to 3, and $R^6$ represents hydrogen or methyl, "g" is an integer from 1 to 70, and "h" is an integer from 1 to 5, and the expoxides thereof obtained by reaction with an expoxide of the formula

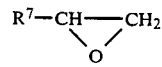

wherein $R^7$ is hydrogen, alkyl having 1 to 10 carbon atoms, aryl having 6 to 14 carbon atoms or alkoxymethyl or alkoxyethyl which each have 1 to 8 carbon atoms in the alkoxy radical.

The formlae of the products of the epoxidation are shown on the attached sheets of drawings as formula VII, VIII, IX and X.

Further expedient and hence preferable embodiments of the invention are revealed by the following description.

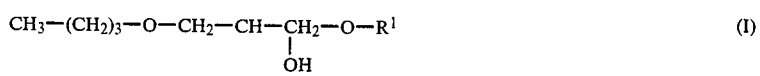 (I)

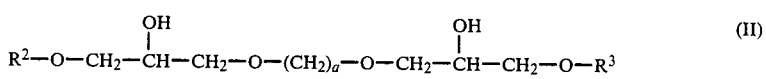 (II)

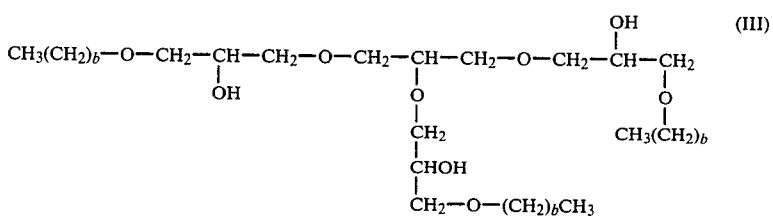 (III)

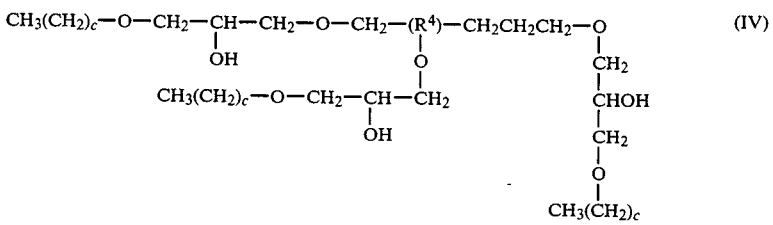 (IV)

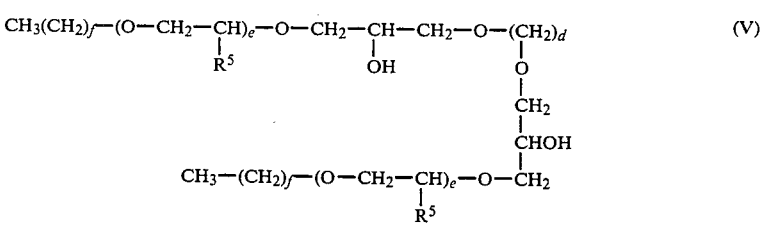 (V)

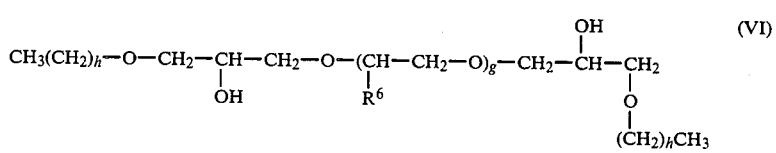 (VI)

wherein
$R^1$ is an alkyl group having at least 8 carbon atoms.
"b" is an integer from 1 to 5,
$R^4$ is an ethylene group and "c" is an integer from 1 to 5, The process of the invention is, in general, characterised in that it uses, in the extraction, aqueous solutions containing at least one liquid polyoxaalkanol, polyoxaalkanediol and/or polyoxaalkanepolyol, which compounds, it turned out, have to have a low solubility in water, preferably a solubility in water which does not exceed 1% by mass at 30° C., and that these compounds have a structural parameter of the type defined which reaches a numerical value of at least 100, while, as a further criterion, the ratio of methylene or optionally substituted methylene groups (—CH(A)—) to ether groups (—O—) is critical and has to be, in general, within the range from about 2.3 to 10. It has been found that on undershooting or overshooting this critical ratio the extractants obtained are not satisfactory.

The solvents used in the process of the invention have to meet certain requirements: they have to be liquid at the extraction temperature and have sufficient affinity for the component to be extracted, i.e. they have to have a very high $K_2$ value which is preferably at least 0.30 and more preferably greater than 0.50 (fluids having $K_2$ values above 0.65 and in particular above 0.75 are outstanding in this respect, as, for example, in the case of the fluid of claim 10, which for this reason and because of the other properties it has been provided with is particularly favourable); the solvent also has to have a very low solubility in the aqueous phase to be extracted, i.e. its solubility should at least not exceed a low threshhold value at a temperature value used during the process of the invention; furthermore, the solvent should not have substantial corrosivity, i.e. it should be virtually non-corrosive, and it has to be largely inert to the components to be extracted, i.e. it should be stable under the extraction conditions. It is moreover advantageous to have an extractant of this type which can be handled without polluting the environment and which can finally be disposed of.

These multiple requirements have to be further widened when a special embodiment of the process necessitates further, i.e. process-specific, criteria.

In an extraction process which is to be used in conjunction with a fermentation process by removing the polar organic compounds formed in the course of fermentation, such as, for example, ethanol, from the mash and recycling the depleted mash without first, i.e. before the extraction, separating off the organisms effecting the fermentation, for example yeasts, the solvent to be used must not exert any toxic effects on the organisms mentioned.

If it is further intended to work up the extract phase obtained, i.e. to separate the extract phase into the reusable solvent and the extracted substance, by means of a membrane-separating process, a solvent (or fluid) suitable for such a purpose should consist of molecules which have a very high molar mass and which, preferably, are additionally very bulky. In separating the extract phase into its components by means of reverse osmosis, the pressure which is necessary on the membrane side and which is determined by the osmotic pressure of the mixture to be separated decreases with increasing mass or molecular size of the solvent. However, even if the separation is performed by means of a solvent diffusion membrane, a large molar mass of the solvent gives improved separating behaviour. If the fluid used has molecules with molar masses of several thousand dalton, it is, finally, possible to work up the extract phases by ultrafiltration. Concerning the technology of the abovementioned separating methods by means of porous and/or semipermeable separating surfaces which can be used according to the invention, compare Ullmann Enzyklopädie der Technischen Chemie [Ullmann's Encyclopaedia of Industrial Chemistry], Volume XVI, page 515, published by Verlag Chemie GmbH, Weinheim, 1978; and R. Rautenbach and R. Albrecht, "Stofftrennung durch Membranen" ["Separating Substances by Means of Membranes"], Chem. Ing. Techn, 54, page 229, 1982.

The requirements of a suitable solvent laid down in the preceding paragraphs appear to be, on the basis of existing knowledge, mutually exclusive in many respects, as an appropriate study of previously customary, commercially available solvents shows.

A large proportion of existing solvents, such as, for example, alcohols, esters and ketones, become solids when their molar mass exceeds 250 g/mol and are therefore disqualified as "potentially liquid" extractants; for instance, tetradecanol, which has a molar mass of only 214 g/mol, has a melting point of only about 40° C., and diphenyl ketone, which has a molar mass of only 182 g/mol, has a melting point of about 49° C.

Other solvents which have a relatively high molar mass, such as, for example, polyethylene glycols or polypropylene glycols, cannot sensibly be used because their solubility in an aqueous medium is too high and, what is more, as the molar mass increases a powerful emulsifying action sets in and makes a separation into an extract phase and an aqueous phase very difficult or industrially even impossible.

Solvents whose solubility in water is very low and which are distinguished at the same time by very high molar masses, such as, for example, silicone oils, have only very low affinity for the polar organic compounds to be extracted; their use would thus make demands on the extraction equipment which, as a consequence of high investment costs, would have to absorb any reduced process costs.

Fluorinated hydrocarbons of the type used in U.S. Pat. No. 4,260,836 and in European Patent Application A 032,445 A2 (publication number; Application No. 81-30,00 97.3) for separating alcohols from their aqueous solutions have, in part, the disadvantage of toxicity and, in part, the disadvantage of corrosivity, but in all the disadvantage of very low affinity for very polar compounds, such as methanol or ethanol.

The pending German Patent Application No. P 31 12 603.0 of the Joint Applicants (our ref. V 277) proposes an extraction process in which the extractants used are preferably alkanols which have 6 to 12 carbon atoms and which distinguish themselves by good affinity for the polar compounds to be extracted, for example ethanol. The polar masses of these extractants, however, are relatively low, namely 102 g/mol for hexanol and 186 g/mol for dodecanol, which is why distillation becomes an attractive option again for isolating the extracted material in the pure state and recovering the solvent. However, the improved alcohol/water ratio in the alcohol/water/solvent system as a result of first carrying out an extraction stage reduces the reflux ratio required, compared with conventional distillation methods, and hence reduces the process heat required for the separation.

A further saving in process energy is possible if a distillative working-up of the extracts can be completely dispensed with by replacing it with a less expensive method, for example with a membrane-separating method. However, if such a process is used solvents having relatively high molar masses are considerably more suitable.

The alcohols mentioned above, except for dodecanol, are frequently disadvantageous because they develop toxic effects on the microorganisms effecting the fermentation. If alcohols having 6 to 11 carbon atoms are to be used as extractants, it is therefore necessary to provide additional, cost-increasing measures in the extraction process to be able to avoid these effects.

The extraction-active component of the fluids according to the invention are the polyoxaalkanols, polyoxaalkanediols and polyoxaalkanepolyols specified in claim 8 by means of the properties profile of claim 8 (a), (b), (c) and (d). "Contains a significant amount" means in this context that the proportion of extraction-active component in the fluid is at least high enough for these compounds to determine the character of the fluid; their proportion preferably amounts to about 90 to 100% by mass.

Table I compares a number of solvents according to the invention with a number of alkanols in terms of their molar masses and their affinity for polar organic compounds.

The measure for affinity is taken to be the partition coefficient for ethanol ($K_2$ value, see Table I) in the water(1)/ethanol(2)/solvent(3) system at an ethanol concentration of 10% by mass, at equal proportions of solvent and water and at a temperature of 30° C.

$K_2$, the partition coefficient, is, in general, defined as follows:

$$K_2 = \frac{\text{Ethanol concentration in the solvent (\% by mass)}}{\text{Ethanol concentration in the water phase (\% by mass)}}$$

where "ethanol" figures as a representative for the polar organic compounds to be extracted. The synthesised compounds mentioned in Table I have been numbered in such a way as to show immediately their membership of the groups of compounds defined in claims 9 to 15, i.e. compound No. 1 satisfies the formula I in which $R^1$ is an alkyl group having 8 to preferably 12 carbon atoms, compound No. 2 satisfies the formula II, and so on (cf. also the working examples below, which illustrate the preferred extraction-active components of the fluids according to the invention and their preparation).

TABLE I

Molar masses and $K_2$ values of alkanols and synthesised solvents $K_2$ is defined as:

$$K_2 = \frac{\text{Ethanol concentration in the solvent (\% by mass)}}{\text{Ethanol concentration in the water phase (\% by mass)}}$$

| | Extractant | Molar mass (g/mol) | $K_2$ value |
|---|---|---|---|
| (a) | alkanols | | |
| | hexanols | 102 | 0.98 |
| | heptanol | 116 | 0.85 |
| | octanol | 130 | 0.74 |
| | nonanol | 144 | 0.64 |
| | decanol | 158 | 0.56 |
| | undecanol | 172 | 0.51 |
| | dodecanol | 186 | 0.47 |
| (b) | synthesised substances | | |
| | No. 1 | 260[a] | 0.43 |
| | No. 2 | 322[a] | 0.86 |
| | No. 3 | 482[a] | 0.65 |
| | No. 4 | 524[a] | 0.70 |
| | No. 5 | 526[a] | 0.73 |
| | No. 6 | 685[b] | 0.62 |
| | No. 7 | 740[a] | 0.50 |
| | No. 8 | 1,394[b] | 0.53 |
| | No. 9 | 2,258[b] | 0.40 |

TABLE I-continued

Molar masses and $K_2$ values of alkanols and synthesised solvents $K_2$ is defined as:

$$K_2 = \frac{\text{Ethanol concentration in the solvent (\% by mass)}}{\text{Ethanol concentration in the water phase (\% by mass)}}$$

| Extractant | Molar mass (g/mol) | $K_2$ value |
|---|---|---|
| No. 10 | 3,380[b] | 0.31 |

[a] confirmed by mass spectrometry
[b] mean molar mass confirmed by cryoscopy

It can be seen from Table I that the fluids according to the invention match the alkanols in their affinity for ethanol, the test substance used, but differ from the alkanols by their markedly higher molar masses, which offer great advantages for a working-up of the extracts by means of membrane-separating techniques.

Extractant No. 5, Table I, which is a member of the preferred group of compounds with the formula V, was subjected to a more indepth examination as a representative for the remainder.

FIG. 1 shows the liquid/liquid equilibrium behaviour of the water(1)/ethanol(2)/solvent(3) system with the solvent No. 5 of Table I at a temperature of 30° C. (atmospheric pressure).

Table II shows the results of an extraction carried out in a pulsed sieve-plate column (lab. scale) using extractant No. 5, preferred by the invention, and indicates the extraction parameters.

The low efficiency of an actual exchange stage can be explained on the basis of the operating conditions (low flow rates, and wide droplet size distribution spectrum) and the resulting very strong back mixing.

TABLE II

Extraction by means of pulsed sieve-plate column (lab. scale)

| Column data | |
|---|---|
| Number of actual plates: | 20 |
| Number of theoretical separating stages: | about 4 |
| Distance between plates: | 54 mm |
| Internal column diameters: | 15 mm |
| Hole diameter: | 1.4 mm |
| Number of holes per plates: | 24 |
| Diameter of guide axis: | 6.1 mm |
| Opening ratio: | 27% |
| Operating method | |
| System: | water(1)/ethanol(2)/fluid No. 5(3) |
| Extraction temperature: | 70° C. |
| Pulsation intensity: | 500 mm · min$^{-1}$ |
| Extractant feed rate: | 260 ml · h$^{-1}$ |
| Water/ethanol phase feed rate: | 290 ml · h$^{-1}$ |
| Density of extractant: | 1.06 g/ml |
| Density of water/ethanol phase: | 0.99 g/ml |
| Phase ratio: | 0.933 |
| Ethanol concentration in the feed: | 6.7% |
| Ethanol concentration of the discharges: | |
| (a) raffinate phase | 2.4% by mass |
| (b) extract phase | 4.0% by mass |

This experiment demonstrates that using a polyoxa[poly]ol markedly depletes the aqueous phase of ethanol to an extent which rivals that obtained when hexanol is used as extractant.

The solvents, nevertheless, also meet the other demands placed on them: while keeping to the limits defined in claims 1 to 8 for the parameter of $K_Z$ defined in claim 1 and for the ratio of —CH(A)— groups to ether groups, they are liquids which are only very sparingly soluble in water. If there is an undershoot of the limits, the solubility in water increases substantially, and if there is an overshoot of the limits, the substances become solids. The fluids have no corrosivity, since, like the polyglycols, which have a very similar chemical structure, they are non-corrosive and can therefore even be used as antifreezes in the cooling water of combustion engines.

Any toxicity of the fluids having molar masses of more than 1000 g/mol against yeasts and bacteria (Lacto bacillae), such as, for example, Saccharomyces cerevisiae, could not be observed, fermentation batches with and without added fluid performing identically. FIGS. II and III show the particular course of fermentation as a function of weight loss due to $CO_2$ fermentation, the rate of $CO_2$ formation automatically measured as weight loss of a defined fermentation batch at 36° C. having been plotted in gramme on the ordinate versus the time in hours (abscissae).

The suitability of the fluids according to the invention for making it possible to work up the extracts by means of a membrane-separating process was investigated on the example of fluid No. 9 of Table I, which is preferred by the invention. The extract obtained by extraction with this fluid in a pulsed sieve-plate column was subjected to membrane filtration; the separating limit of the membrane used was given as a molar mass of 500. The filtrate consisted of 60% by mass of ethanol and 40% by mass of water, no residual fluid being detectable therein.

The invention consequently provides in the form of the polyoxaalkanols, polyoxaalkanediols and polyoxaalkanepolyols of the invention, new potential solvents which meet all requirements for the extraction process of the invention.

PREPARATION OF FLUIDS

All the fluids can be prepared by the addition, known per se, of hydroxy compounds onto epoxides under the catalytical action of Lewis acids (Houben-Weyl: Methoden der Organ. Chemie [Methods of Organic Chemistry], Volume 6/3, page 40, 4th edition, published by Georg Thieme Verlag, Stuttgart, 1965).

In preparing "simple", only slightly branched, fluids, it is easily possible, by means of control measures known from the art of organic syntheses (such as, for example, by working with a high excess of one component), to obtain pure defined compounds. This is demonstrated by recording IR and mass spectra and by determining the molar masses. To obtain fluids with a more complex structure in the pure form has in general proved more difficult, but is usually not necessary for the purposes of the process according to the invention.

If the synthesis starts from commercially available polyglycols (for example PEG 300 or PPG 2,000), this gives fluids which are composed of several types of molecule, since the starting compounds themselves are mixtures whose individual members, it is true, belong to the same class of compound, but which, in their molar mass, fluctuate about the stated mean (for example 300 or 2,000). The invention therefore makes use not only of the defined individual compounds but also of such mixtures.

Even in the case of the highly branched polyoxapolyols (formulae VII to X), the synthesis produces mixtures which in the main consist of isomers of the empirical formulae stated.

However, this does not impair the usefulness of the fluids for the process according to the invention, since the extraction behaviour and the separability by membrane filtration are virtually unaffected by the position of the side chains in the molecule.

According to the invention, it has been found that the fluids characterised in claim 16 by their method of preparation are the best at displaying the multiple, combined properties desired for the process according to the invention for the extraction and the subsequent working-up.

Preferred fluids, and their preparation, will now be illustrated with reference to Table I.

INDIVIDUAL COMPOUNDS OF TABLE I (1) Re solvent No. 1

130 g (1 mol) of butyl glycidyl ether are added dropwise with stirring to 520 g (4 mol) octan-1-ol which contains 1.3 g (5 mmol) of tin(IV) chloride as a catalyst. The reaction sets in spontaneously, accompanied by a marked increase in temperature. After the dropwise addition is complete, the mixture is held at 90° C. for 1 hour, is then neutralised by adding pulverulent calcium carbonate, and is filtered, and the filtrate is freed from excess octanol by vacuum distillation to give, in yields of 98 to 100%, solvent No. 1, which has the formula:

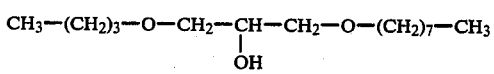

$M = 260$ g/mol
$\rho = 0.9040$ g/ml
$K_2 = 0.43$; C:O ratio = 7.5:1
$K_Z = 116$ (2) Re solvent No. 2

202 g (1 mol) of butanediol diglycidyl ether are added dropwise with stirring to 600 g (10 mol) of propan-1-ol which contains 1.3 g (5 mmol) of tin(IV) chloride. The procedure described under (1) is then followed to give solvent No. 2 of the formula:

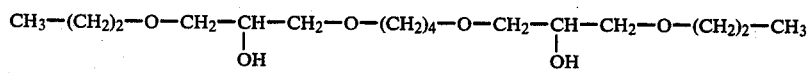

$M = 332$ g/mol
$\rho = 1.0336$ g/ml
$K_2 = 0.86$; C:O ratio = 4.5:1
$K_Z = 102$ (3) Re solvent No. 3

195 g (1.5 mol) of butyl glycidyl ether are added dropwise with stirring to 46 g (0.5 mol) of glycerol which contains 0.8 g of tin(IV) chloride, and the procedure then followed is as described under (1). When the mixture has been filtered, it is, unlike in (1), extracted several times with water to remove any unconverted glycerol present, and the product is then freed from water by distillation to give solvent No. 3 of the formula

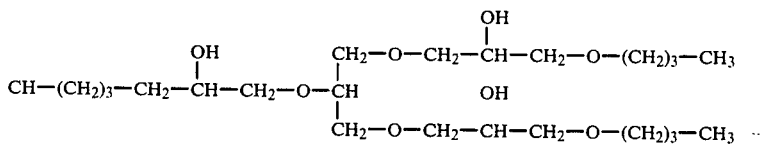

M = 482 g/mol
ρ = 1.0289 g/ml
$K_2$ = 0.65; C:O ratio = 4:1
$K_Z$ = 124

(4) Re solvent No. 4

195 g (1.5 mol) of butyl glycidyl ether are added dropwise with stirring to 67 g (0.5 mol) of hexane-1,2,6-triol which contains 0.8 g of tin(IV) chloride, and the procedure then followed is as described under (3) to give solvent No. 4 of the formula:

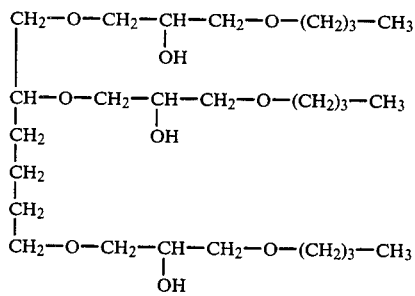

M = 524 g/mol
ρ = 1.0301 g/ml
$K_2$ = 0.70; C:O ratio = 4.5:1
$K_Z$ = 135

(5) Re solvent No. 5

202 g (1 mol) of butanediol diglycidyl ether are added dropwise with stirring to 810 g (5 mol) of diethylene glycol monobutyl ether which contains 1.56 g (6 mmol) of tin(IV) chloride. The procedure then followed is as described under (1), to give solvent No. 5 of the formula

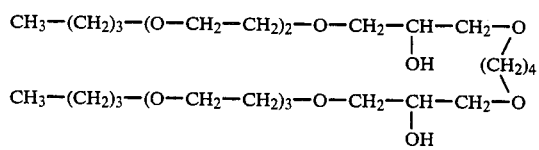

M = 526 g/mol
ρ = 1.0573 g/ml
$K_2$ = 0.73; C:O ratio = 3.25:1
$K_Z$ = 124

(6) Re solvent No. 6

153 g (1.2 mol) of butyl glycidyl ether are added dropwise to 250 g (0.6 mol) of polypropylene glycol 425 which contains 0.66 g of anhydrous aluminium chloride, and the procedure then followed is as described under (3), to give solvent No. 6 of the formula

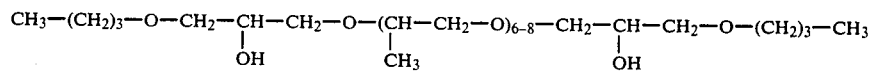

φM = 685 g/mol
ρ = 1.0226 g/ml
$K_2$ = 0.73; C:O ratio = 2.8:1
$K_Z$ = 146

(7) Re solvent No. 7

First the hexanetriol derivative is prepared as described under (4) and, when the formation reaction has ended, reacted without prior isolation with three times the molar amount of 1,2-epoxybutane. The reaction product is isolated in the usual manner by extraction with water and subsequent vacuum distillation. This gives the extraction fluid No. 7 of the general empirical formula

| | $C_{39}H_{77}O_9(OH)_3$ |
|---|---|
| M = 740 g/mol | $K_2$ = 0.50; C:O ratio = 4.3:1 |
| ρ = 1.00921 g/ml | $K_Z$ = 161 |

(8) Re solvent No. 8

18.2 g of sorbitol (0.1 mol) are suspended in 250 ml of ethylene glycol dimethyl ether which contains 0.5 g of tin(IV) chloride. 78 g (0.6 mol) of butyl glycidyl ether are then added dropwise to form a colourless solution which is then reacted with 43.2 g (0.6 mol) of epoxybutane. Working up as described under (7) gives an extraction fluid of the general empirical formula

| | $C_{72}H_{140}O_{18}(OH)_6$ |
|---|---|
| M = 1,394 g/mol | $K_2$ = 0.53; C:O ratio = 4:1 |
| ρ = 1.0024 g/ml | $K_Z$ = 215 |

(9) Re solvent No. 9

The reaction product obtained in (8) is reacted with a further 86.4 g (1.2 mol) of 1,2-epoxybutane to give an extraction fluid of the general empirical formula

| | $C_{120}H_{236}O_{30}(OH_6)$ |
|---|---|
| M = 2,258 g/mol | $K_2$ = 0.30; C:O ratio = 4:1 |
| ρ = 0.9938 g/ml | $K_Z$ = 278 |

(10) Re solvent No. 10

200 g (about 0.1 mol) of polypropylene glycol 2,000 are eluted with 250 ml of ethylene glycol dimethyl ether, about 1.3 g of tin(IV) chloride are added, and the mixture is then reacted with stirring with 52 g (0.4 mol) of butyl glycidyl ether. After the reaction has ended, 86.8 g (1.2 mol) of 1,2-epoxybutane are added dropwise.

The customary working up gives extraction fluid No. 10 which has a mean molar mass of 3,380 g/mol.

$\emptyset M = 3,380$ g/mol
$\rho = 0.9936$ g/ml
$K_2 = 0.31$
C:O ratio 2.7:1

Further details on compounds Nos. 7 to 10, which have the corresponding formulae VII, VIII, IX and X, have been put together below. These compounds represent preferred members of compounds according to claim 15.

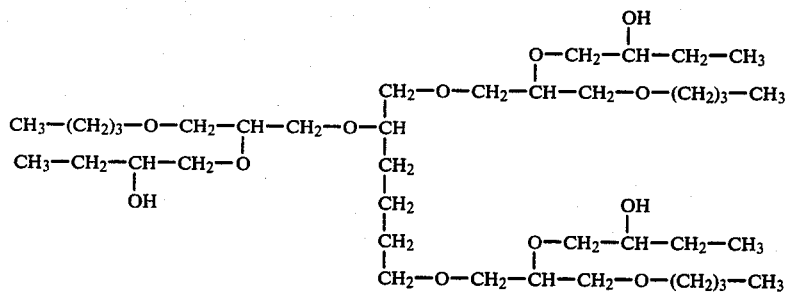

Formula VII in respect of Claim 15
M = 740 g/mol; $K_2 = 0.50$; $K_Z = 161$; C:O ratio = 4.33:1
General formula: $C_{39}H_{77}O_9(OH)_3$

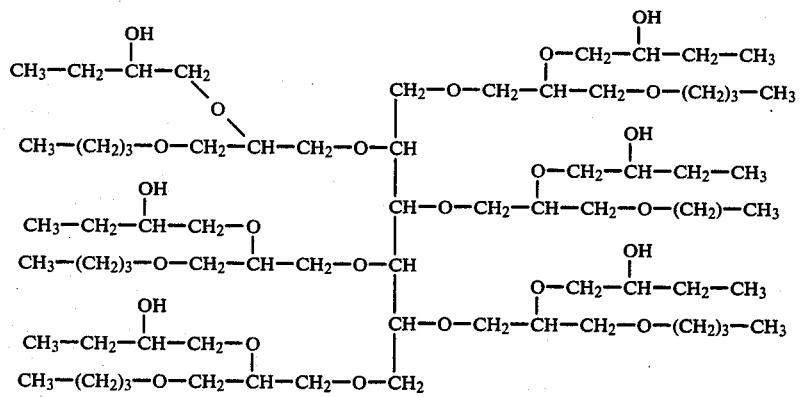

Formula VIII in respect of Claim 15
M = 1,394 g/mol; $K_2 = 0.53$; $K_Z = 215$; C:O ratio = 4.1
General formula: $C_{72}H_{140}O_{18}(OH)_6$ $K_Z = 325$.

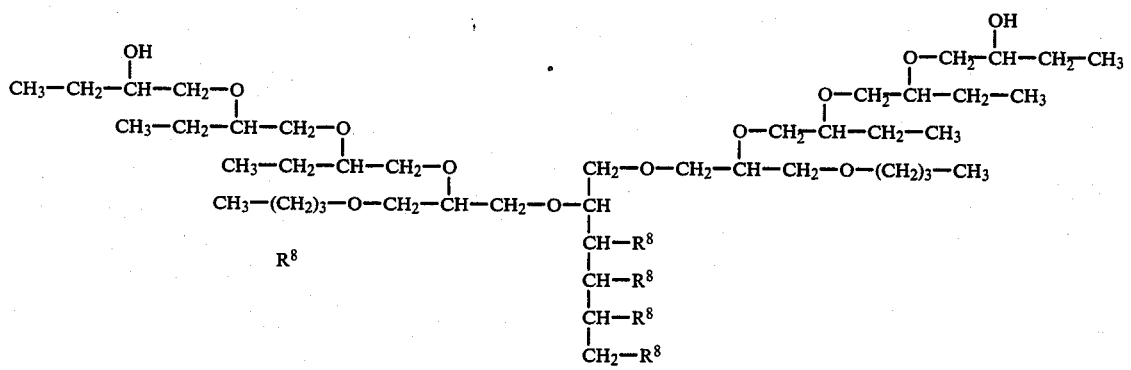

Formula IX in respect of Claim 15
M = 2,258 g/mol; $K_2 = 0.40$; $K_Z = 278$; C:O ratio = 4:1
General formula: $C_{120}H_{236}O_{30}(OH)_6$

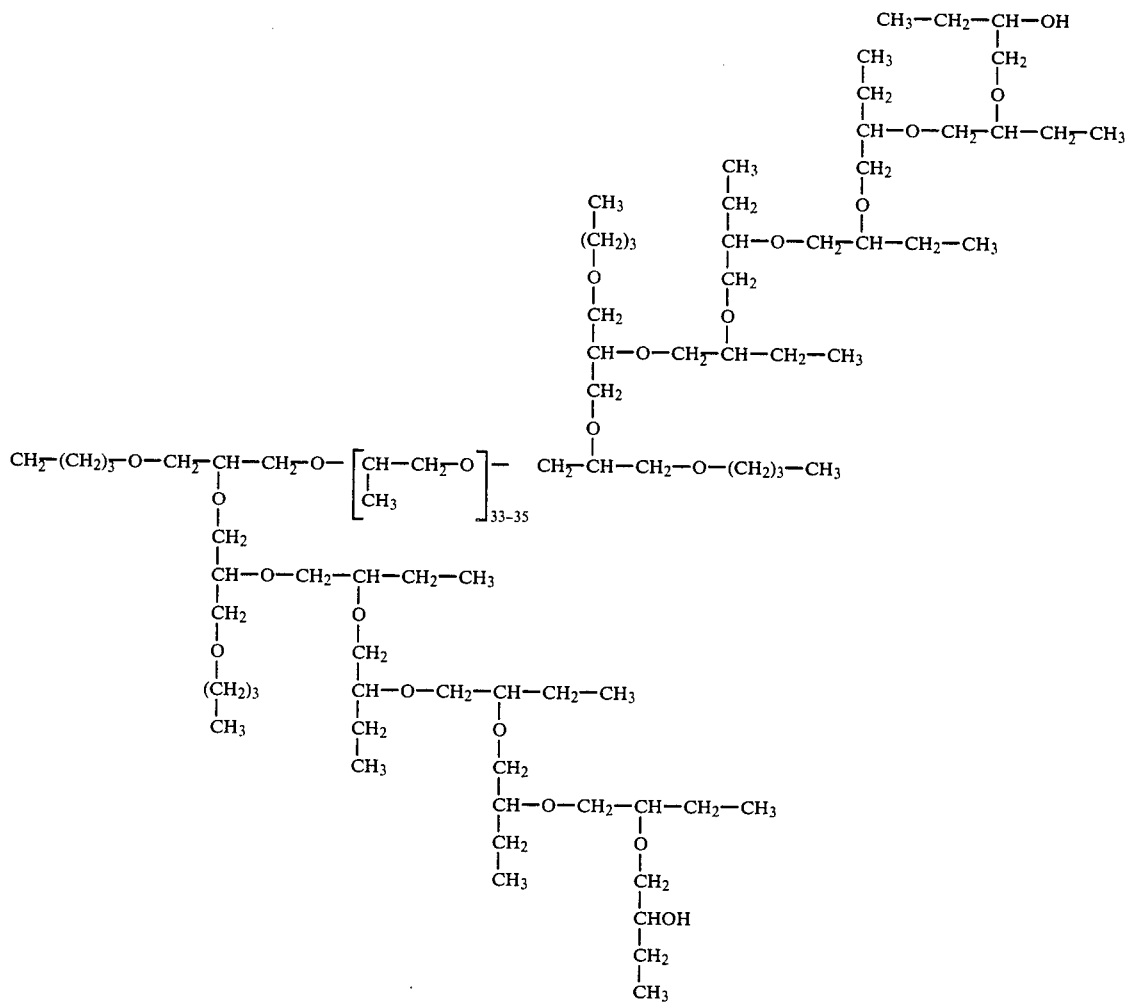

Formula X in respect of Claim 15
M = 3,380 g/mol; K₂ = 0.31; K_Z = 325
C:O ratio = 2.7:1

I claim:

1. A process for separating polar organic compounds, in particular lower aliphatic alcohols, from their aqueous solutions by extracting the aqueous solution with a liquid extractant and separating the polar organic compound from the extract, wherein the aqueous solution is extracted with at least one liquid polyoxaalkanol, polyoxaalkanediol and/or polyoxaalkanepolyol which has a low solubility in water at 30° C., namely of less than 1% by mass, and a parameter, $K_Z$, which has a numerical value of at least 100 and is defined by the following equation:

$$K_Z = \frac{M}{\sqrt{2o + oh}}$$

in which "M" denotes the molar mass which is greater than 250 g/mol, "o" denotes the number of ether groups and "oh" denotes the number of hydroxyl groups, and in which compounds the numerical ratio of —CH(A)— groups to ether groups is within the range from about 2.3:1 to 10:1, where A represents hydrogen, CH₃ and/or OH.

2. A process according to claim 1, wherein the extractant used is at least one compound of the general formula

Y'—O—X—O—Y"

in which

X is an at least divalent polyalkylene or polyoxaalkylene radical which has a total of 2 to about 140 carbon atoms in the skeleton chain and which has been substituted by one or more hydroxyl groups, alkoxyl groups and/or hydroxyalkoxyl groups which each have 1 to about 7 carbon atoms and/or glycidyl groups and is optionally additionally substituted by one or more lower alkyl groups and in which the individual alkylenes of the skeleton chain can be identical or different and contain 2 to 6 carbon atoms, and Y' and Y" can be identical or different and independently of each other denote alkyl groups having 1 to 12 carbon atoms and/or cycloalkyl groups having 3 to 10 carbon atoms and/or aryl groups having 6 to 14 carbon atoms.

3. A process according to claim 1, wherein the extractant used contains a compound of the formula I

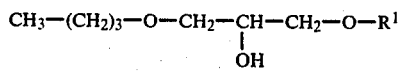

in which $R^1$ is an alkyl group having at least 8 carbon atoms.

4. A process according to claim 1, wherein the extractant used contains a compound of the formula II

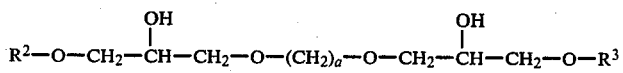

in which $R^2$ and $R^3$ are identical or different and independently of each other denote alkyl or cycloalkyl groups which each have 3 to 10 carbon atoms, or aryl groups having 6 to 14 carbon atoms, and "a" is an integer within the range from 2 to 6.

5. A process according to claim 1, wherein the extractant used contains a compound of the formula III

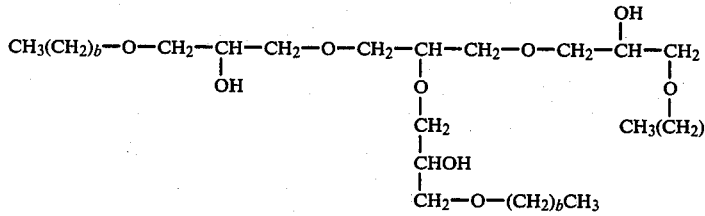

in which "b" is an integer from 1 to 5.

6. A process according to claim 1, wherein the extractant used contains a compound of the formula IV

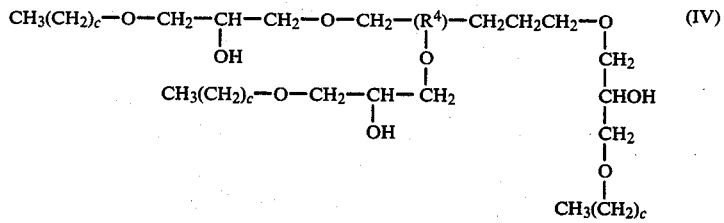

in which $R^4$ is an ethylene group and "c" is an integer from 1 to 5.

7. A process according to claim 1, wherein the extractant used contains a compound of the formula V

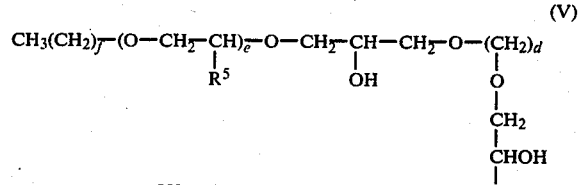

in which $R^5$ is hydrogen or methyl, "d" is an integer from 2 to 6, "e" is an integer from 1 to 7, and "f" is an integer from 0 to 3.

8. A process according to claim 1, wherein the extractant used contains a compound of the formula VI

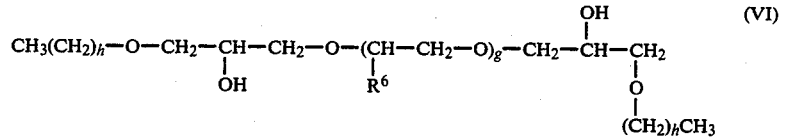

in which $R^6$ represents hydrogen or methyl, "g" is an integer from 1 to 70, and "h" is an integer from 1 to 5.

9. A process for separating polar organic compounds, in particular lower aliphatic alcohols, from their aqueous solutions by extracting the aqueous solution with a liquid extractant and separating the polar organic compound from the extract, wherein the aqueous solution is extracted with at least one liquid polyoxaalkanol, polyoxaalkanediol and/or polyoxaalkanepolyol which has a low solubility in water, namely of less than 1% by mass, and a parameter, $K_Z$, which has a numerical value of at least 100 and is defined by the following equation:

$$K_Z = \frac{M}{\sqrt{2o + oh}}$$

in which "M" denotes the molar mass, "o" denotes the number of ether groups and "oh" denotes the number of hydroxyl groups, and in which compounds the numerical ratio of —CH(A)— groups to ether groups is within the range from about 2.3:1 to 10:1, where A represents hydrogen, CH$_3$ and/or OH, which extractant used has been obtained by epoxidising at least one of the compounds of the formulae I, II, III, IV, V, and VI named in claims 3 to 8 with an epoxide of the formula

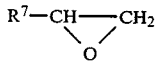

in which R$^7$ is hydrogen, alkyl having 1 to 10 carbon atoms, aryl having 6 to 14 carbon atoms or alkoxymethyl or alkoxyethyl which each have 1 to 8 carbon atoms in the alkoxy radical.

10. A process for separating polar organic compounds, in particular lower aliphatic alcohols, from their aqueous solutions by extracting the aqueous solution with a liquid extractant and separating the polar organic compound from the extract, wherein the aqueous solution is extracted with at least one liquid polyoxaalkanol, polyoxaalkanediol and/or polyoxaalkanepolyol which has a low solubility in water, namely of less than 1% by mass, and a parameter, K$_Z$, which has a numerical value of at least 100 and is defined by the following equation:

$$K_Z = \frac{M}{\sqrt{2o + oh}}$$

in which "M" denotes the molar mass, "o" denotes the number of ether groups and "oh" denotes the number of hydroxyl groups, and in which compounds the numerical ratio of —CH(A)— groups to ether groups is within the range from about 2.3:1 to 10:1, where A represents hydrogen, CH$_3$ and/or OH, which polyoxaalkanol, polyoxaalkanediol and polyoxaalkanepolyol has been obtained by reacting (a) at least one hydroxy compound selected from the group comprising alkanols having 1 to 12 carbon atoms, alkanediols having 2 to 6 carbon atoms, C$_3$–C$_6$-alkanetriols, C$_4$–C$_6$-alkanetetrols, C$_5$–C$_6$-alkanepentols, C$_6$-alkanehexols, polyethylene glycols, polypropylene glycols and polyethylenepropylene glycols having on average 2 to about 70 oxaalkylene units, with (b) at least one epoxide of the formula

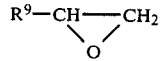

in which R$^9$ represents hydrogen, alkyl having 1 to 10 carbon atoms, aryl having 6 to 14 carbon atoms, alkoxymethyl or alkoxyethyl which each have 1 to 8 carbon atoms in the alkoxy radical, or with a C$_2$–C$_8$-alkanediol diglycidyl ether, using (c) a ratio of OH groups to epoxy groups of about 1:1, in the presence of (d) Lewis acid catalysts such as SnCl$_4$ or AlCl$_3$.

11. A process according to claim 1, wherein the aqueous solution is extracted at temperatures within the range from 25° C. to 120° C.

12. A process according to claim 1, wherein the extracted polar organic compound in the extract is separated from the extractant without using a thermal separating process.

13. A process according to claim 1, wherein the polar organic compounds are separated from the extractant by a membrane-separating process.

14. A process according to claim 1, wherein the polar organic compounds are the main product in continuous or discontinuous fermentation and they are extracted out of the fermentation liquid and the depleted solution is returned to the fermentation step.

15. A process according to claim 1, wherein the polar organic compounds are separated from the fermentation liquid without separating off beforehand the microorganisms effecting the fermentation.

16. A process according to claim 11, wherein the polar organic compounds are the main product of a continuous or discontinuous fermentation and are extracted out of the fermentation liquor and the depleted solution returned to the fermentation step.

17. A process according to claim 1, wherein the polar organic compound is an alcohol.

* * * * *